US006833368B2

United States Patent
Murphy et al.

(10) Patent No.: US 6,833,368 B2
(45) Date of Patent: Dec. 21, 2004

(54) 1, 2, 5, 10-TETRAHYDROPYRIDAZINO[4, 5-B]QUINOLINE-1,10-DIONES AND THEIR USE FOR THE TREATMENT OF PAIN

(75) Inventors: Megan Murphy, Wilmington, DE (US); Wenhua Xiao, Wilmington, DE (US); Dean Gordon Brown, Wilmington, DE (US); Rebecca Ann Urbanek, Wilmington, DE (US); Frances Marie McLaren, Wilmington, DE (US); Edward Vacek, Wilmington, DE (US); Thomas Bare, West Chester, PA (US); Carey Lynn Horchler, Wilmington, DE (US); Christine Barlaam, Reims (FR); Gary Banks Steelman, Wilmington, DE (US); Vernon Alford, Raritan, NJ (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/381,915

(22) PCT Filed: Sep. 28, 2001

(86) PCT No.: PCT/SE01/02123

§ 371 (c)(1),
(2), (4) Date: Oct. 9, 2003

(87) PCT Pub. No.: WO02/26738

PCT Pub. Date: Apr. 4, 2002

(65) Prior Publication Data

US 2004/0058927 A1 Mar. 25, 2004

Related U.S. Application Data

(60) Provisional application No. 60/236,629, filed on Sep. 29, 2000.

(51) Int. Cl.$^7$ .................. C07D 471/04; A61K 31/5025; A61P 25/04

(52) U.S. Cl. ...................................... 514/248; 544/234

(58) Field of Search ......................... 544/234; 514/248

(56) References Cited

FOREIGN PATENT DOCUMENTS

| EP | 0736531 | 10/1996 |
|---|---|---|
| WO | WO 9511244 | 4/1995 |
| WO | WO 0147523 | 7/2001 |
| WO | WO 0147524 | 7/2001 |
| WO | WO 0147824 | 7/2001 |
| WO | WO 0147923 | 7/2001 |
| WO | WO 0147925 | 7/2001 |

*Primary Examiner*—Venkataraman Balasubramanian
(74) *Attorney, Agent, or Firm*—Kenneth F. Mitchell

(57) ABSTRACT

Compounds useful for the treatment of pain in accord with structural diagram (I), or tautomers or pharmaceutically-acceptable salts of such compounds, wherein R$^1$ and A are as disclosed in the specification. Also disclosed are methods for the treatment of pain using compounds according to structural diagram (I) and pharmaceutical compositions comprising compounds according to structural diagram (I).

9 Claims, No Drawings

1, 2, 5, 10-TETRAHYDROPYRIDAZINO[4, 5-B]QUINOLINE-1,10-DIONES AND THEIR USE FOR THE TREATMENT OF PAIN

This application is a 371 of PCT/SE01/02123 filed Sep. 28, 2001, which claims benefit of U.S. Provisional Application No. 60/236,629, filed Sep. 29, 2000.

FIELD OF THE INVENTION

This invention relates to the treatment or prevention of pain or nociception.

RELATED ART

Pain is a sensory experience distinct from sensations of touch, pressure, heat and cold. It is often described by sufferers by such terms as bright, dull, aching, pricking, cutting or burning and is generally considered to include both the original sensation and the reaction to that sensation. This range of sensations, as well as the variation in perception of pain by different individuals, renders a precise definition of pain difficult, however, many individuals suffer with severe and continuous pain.

Pain that is caused by damage to neural structures is often manifest as a neural supersensitivity or hyperalgesia and is termed "neuropathic" pain. Pain can also be "caused" by the stimulation of nociceptive receptors and transmitted over intact neural pathways, such pain is termed "nociceptive" pain.

The level of stimulation at which pain becomes noted is referred to as the "pain threshold." Analgesics are pharmaceutical agents which relieve pain by raising the pain threshold without a loss of consciousness. After administration of an analgesic drug a stimulus of greater intensity or longer duration is required before pain is experienced. In an individual suffering from hyperalgesia an analgesic drug may have an anti-hyperalgesic effect. In contrast to analgesics, agents such as local anaesthetics block transmission in peripheral nerve fibers thereby blocking awareness of pain. General anaesthetics, on the other hand, reduce the awareness of pain by producing a loss of consciousness.

Tachykinin antagonists have been reported to induce antinociception in animals, which is believed to be analogous to analgesia in man (Maggi et al, J. Auton. Pharmacol. (1993) 13, 23–93). In particular, non-peptide NK-1 receptor antagonists have been shown to produce such analgesia. For example, the NK-1 receptor antagonist RP 67,580 produced analgesia with potency comparable to that of morphine (Garret et al, Proc. Natl. Acad. Sci. USA (1993) 88, 10208–10212).

The opioid analgesics are a well-established class of analgesic agents with morphine-like actions. Synthetic and semi-synthetic opioid analgesics are derivatives of five chemical classes of compound: phenanthrenes; phenylheptylamines; phenylpiperidines; morphinans; and benzomorphans. Pharmacologically these compounds have diverse activities, thus some are strong agonists at the opioid receptors (e.g. morphine); others are moderate to mild agonists (e.g. codeine); still others exhibit mixed agonist-antagonist activity (e.g. nalbuphine); and yet others are partial agonists (e.g. nalorphine). Whilst an opioid partial agonist such as nalorphine, (the N-alkyl analogue of morphine) will antagonize the analgesic effects of morphine, when given alone it can be a potent analgesic in its own right.

Of all of the opioid analgesics, morphine remains the most widely used, but, in addition to its therapeutic properties, it has a number of drawbacks including respiratory depression, decreased gastrointestinal motility (resulting in constipation), nausea and vomiting. Tolerance and physical dependence also limit the clinical uses of opioid compounds.

Aspirin and other salicylate compounds are frequently used in treatment to interrupt amplification of the inflammatory process in rheumatoid diseases and arthritis and temporarily relieve the pain. Other drug compounds used for these purposes include phenylpropionic acid derivatives such as Ibuprofen and Naproxen, Sulindac, phenyl butazone, corticosteroids, antimalarials such as chloroquine and hydroxychloroquine sulfate, and fenemates (J. Hosp. Pharm., 36:622 (May 1979)). These compounds, however, are ineffective for neuropathic pain.

Available therapies for pain also have drawbacks. Some therapeutic agents require prolonged use before an effect is experienced by the patient. Other existing drugs have serious side effects in certain patients, and subjects must be carefully monitored to ensure that any side effects are not unduly threatening. Most existing drugs provide only temporary relief from pain and must be taken consistently on a daily or weekly basis. With disease progression the amount of medication needed to alleviate the pain often increases, thus increasing the potential for adverse side effects.

NMDA receptors are defined by the binding of N-methyl-D-aspartate (NMDA) comprise a receptor/ion channel complex with several different identified binding domains. NMDA itself is a molecule structurally similar to glutamate (Glu) which binds at the glutamate binding suite and is highly selective and potent in activating the NMDA receptor (Watkins (1987); Olney (1989)).

Many compounds are known that bind at the NMDA/Glu binding site (for example CPP, DCPP-ene, CGP 40116, CGP 37849, CGS 19755, NPC 12626, NPC 17742, D-AP5, D-AP7, CGP 39551, CGP-43487, MDL-100,452, LY-274614, LY-233536, and LY233053). Other compounds, referred to as non-competitive NMDA antagonists, bind at other sites in the NMDA receptor complex (examples are phencyclidine, dizocilpine, ketamine, tiletamine, CNS 1102, dextromethorphan, memantine, kynurenic acid, CNQX, DNQX; 6,7-DCQX, 6,7-DCHQC, R(+)-HA-966, 7-chlorokynurenic acid, 5,7-DCKA, 5-iodo-7-chloro-kynurenic acid, MDL-28,469, MDL-100,748, MDL-29,951, L-689,560, L-687,414, ACPC, ACPCM, ACPCE, arcaine, diethylenetriamine, 1,10-diaminodecane, 1,12-diaminododecane, ifenprodil, and SL-82.0715). These compounds have been extensively reviewed by Rogawski (1992) and Massieu et. al., (1993), and articles cited therein.

In addition to its physiological function, glutamate (Glu) can be neurotoxic. Glu neurotoxicity is referred to as "excitotoxicity" because the neurotoxic action of Glu, like its beneficial actions, is mediated by an excitatory process (Olney (1990); Choi (1992)). Normally, when Glu is released at a synaptic receptor, it binds only transiently and is then rapidly removed from the receptor by a process that transports it back into the cell. Under certain abnormal conditions, including stroke, epilepsy and CNS trauma, Glu uptake fails and Glu accumulates at the receptor resulting in a persistent excitation of electrochemical activity that leads to the death of neurons that have Glu receptors. Many neurons in the CNS have Glu receptors, so excitotoxicity can cause an enormous amount of CNS damage.

Acute excitotoxicity injury can occur as a result of ischemic events, hypoxic events, trauma to the brain or spinal cord, certain types of food poisoning which involve an excitotoxic poison such as domoic acid, and seizure-mediated neuronal degeneration, which can result from persistent epileptic seizure activity (status epilepticus). A large body of evidence has implicated the NMDA receptor as one receptor subtype through which Glu mediates a substantial amount of CNS injury, and it is well established that NMDA antagonists are effective in protecting CNS neurons against excitotoxic degeneration in these acute CNS injury syndromes (Choi (1988); Olney (1990)).

In addition to neuronal damage caused by acute insults, excessive activation of Glu receptors may also contribute to more gradual neurodegenerative processes leading to cell death in various chronic neurodegenerative diseases, including Alzheimer's disease, amyotrophic lateral sclerosis, AIDS dementia, Parkinson's disease and Huntington's disease (Olney (1990)). It is generally considered that NMDA antagonists may prove useful in the therapeutic management of such chronic diseases.

In the 1980's it was discovered that PCP (also known as "angel dust") acts at a "PCP recognition site" within the ion channel of the NMDA Glu receptor. PCP acts as a non-competitive antagonist that blocks the flow of ions through the NMDA ion channel. More recently it has become evident that drugs which act at the PCP site as non-competitive NMDA antagonists are likely to have psychotomimetic side effects. Further, it is now recognized that certain competitive and non-competitive NMDA antagonists can cause similar pathomorphological effects in rat brain (Olney et. al., (1991); Hargreaves et. al., (1993)). Such compounds also have psychotomimetic effects in humans (Kristensen et. al., (1992); Herrling (1994); Grotta (1994)).

The glycine binding site of the NMDA receptor complex is distinguishable from the Glu and PCP binding sites. Also, it has recently been discovered that NMDA receptors occur as several subtypes which are characterized by differential properties of the glycine binding site of the receptor. Many compounds that bind at the NMDA receptor glycine site, useful for the treatment of stroke and neurodegenerative conditions, have been described in U.S. Pat. Nos. 5,604,227; 5,733,910; 5,599,814; 5,593,133; 5,744,471; 5,837,705 and 6,103,721.

SUMMARY OF THE INVENTION

It has now been discovered that certain compounds which exhibit the property of binding to the NMDA receptor glycine site have utility for the amelioration of pain and particularly for the amelioration of neuropathic pain.

In a first aspect the present invention provides compounds of structural diagram I

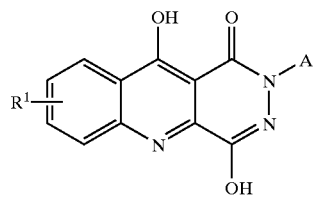

or tautomers or a pharmaceutically-acceptable salts thereof, useful for the treatment of pain, wherein:

$R^1$ is halo;

A is selected from compounds according to structural diagrams II, III, IV and V

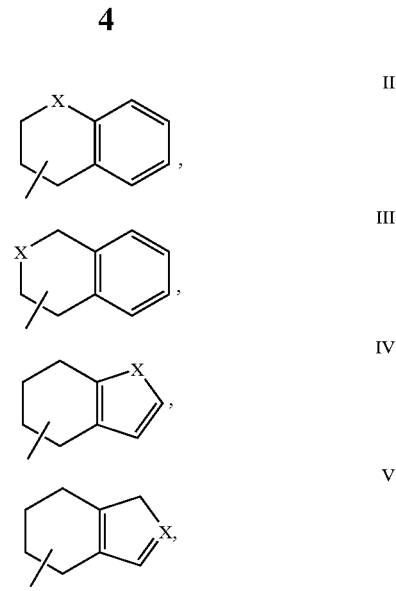

wherein X is selected from carbon, oxygen and sulfur.

Particular embodiments of the invention provide compounds according to structural diagrams VI or VII

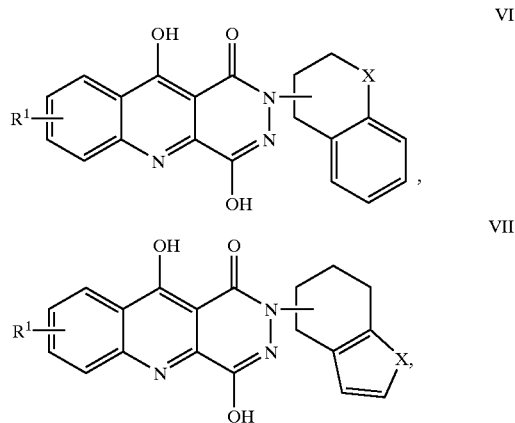

wherein $R^1$ and X are as defined heretofore.

More particular embodiments of the invention provide compounds according to structural diagrams VIII or IX:

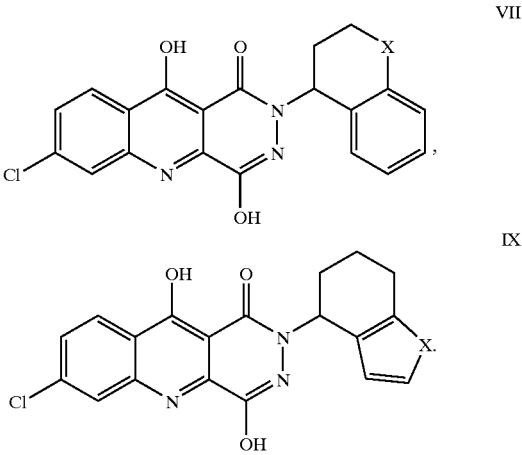

Still more particular embodiments of the invention are compounds selected from:

7-chloro-4-hydroxy-2-(2H,3H,4H-benzo[e]thian-4-yl)-1,2,5,10-tetrahydropyridazino[4,5-b]quinoline-1,10-dione;

7-chloro-4-hydroxy-2-(chroman-4-yl)-1,2,5,10-tetrahydropyridazino[4,5-b]quinoline-1,10-dione;

7-chloro-4-hydroxy-2-(4,5,6,7-tetrahydrobenzo[b]thiophen-4-yl)-1,2,5,10-tetrahydropyridazino[4,5-b]quinoline-1,10-dione, and 7-chloro-4-hydroxy-2-(1,2,3,4-tetrahydronaphthyl)-1,2,5,10-tetrahydropyridazino[4,5-b]quinoline-1,10-dione.

In a second aspect the invention provides a method for the treatment of pain comprising administering to a subject suffering from pain a pain-ameliorating effective amount of any compound according to structural diagram I. A particular embodiment of the invention provides a method for the treatment of neuropathic pain.

Particular embodiments of the method provided herein comprises administering pain-ameliorating effective amounts of compounds according to structural diagram VI or VII as defined heretofore.

Another aspect of the invention is a method for making compounds in accord with structural diagram I.

Yet other aspects of the invention are pharmaceutical compositions which contain a compound in accord with structural diagram I; the use of compounds in accord with structural diagram I for the preparation of medicaments and pharmaceutical compositions, and a method comprising binding a compound of the invention to the NMDA receptor glycine site of a warm-blooded animal, such as a human being, so as to beneficially inhibit the activity of the NMDA receptor.

DETAILED DESCRIPTION OF THE INVENTION

Compounds of the invention are those within the scope of the generic description and particularly those compounds exemplified hereafter.

Suitable pharmaceutically-acceptable salts of compounds of the invention include acid addition salts such as methanesulphonate, fumarate, hydrochloride, hydrobromide, citrate, tris(hydroxymethyl)aminomethane, maleate and salts formed with phosphoric and sulphuric acid. In other embodiments, suitable salts are base salts such as an alkali metal salts for example sodium, alkaline earth metal salts for example calcium or magnesium, organic amine salts for example triethylamine, morpholine, N-methylpiperidine, N-ethylpiperidine, procaine, dibenzylamine, choline, N,N-dibenzylethylamine or amino acids such as lysine.

Another aspect of the invention is a process for making compounds of the invention, which process comprises the following steps:

a) Preparing a Boc-protected hydrazine by reacting an aldehyde, according to one of the procedures shown in the following scheme:

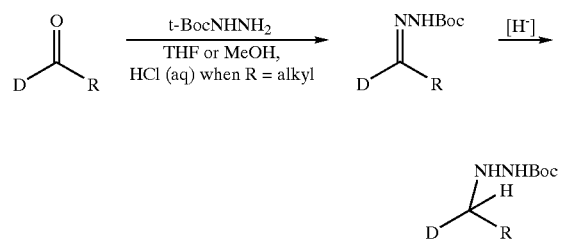

b) coupling said Boc-protected hydrazine and cyclizing the product according to the process of the following scheme to form a compound according to structural diagram I:

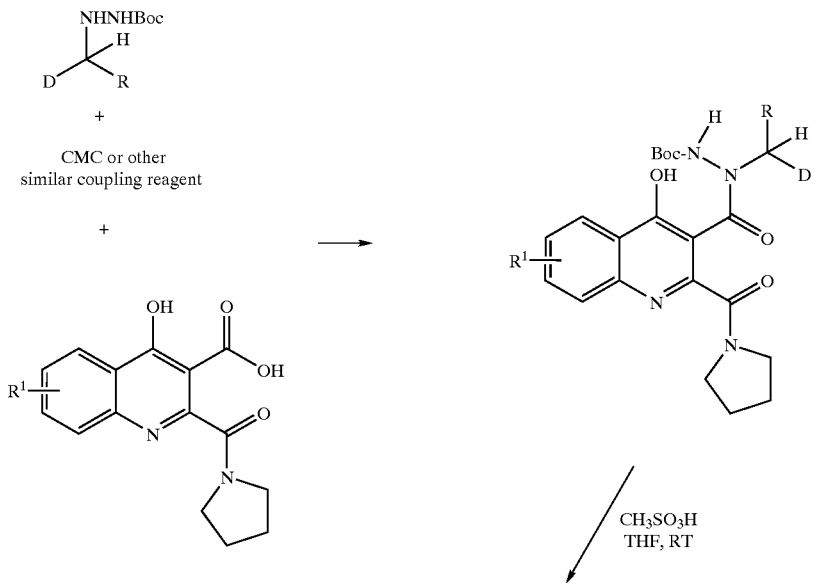

-continued

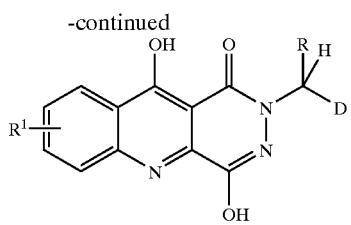

wherein:
CMC is 1-cyclohexyl-3-(2-morpholinoethyl) carbodiimide metho-p-toluenesulfonate;
the "R/H/D" group is the A moiety of structural diagram I; and throughout the foregoing process:
$R^1$ is as defined for structural diagram I.

To use a compound of the invention or a pharmaceutically-acceptable salt thereof for the therapeutic treatment, which may include prophylactic treatment, of pain in mammals, which may be humans, the compound can be formulated in accordance with standard pharmaceutical practice as a pharmaceutical composition.

Suitable pharmaceutical compositions that contain a compound of the invention may be administered in conventional ways, for example by oral, topical, parenteral, buccal, nasal, vaginal or rectal administration or by inhalation. For these purposes a compound of the invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions. A preferred route of administration is orally by tablet or capsule.

In addition to a compound of the present invention a pharmaceutical composition of this invention may also contain one or more other pharmacologically-active agents, or such pharmaceutical composition may be simultaneously or sequentially co-administered with one or more other pharmacologically-active agents.

Pharmaceutical compositions of this invention will normally be administered so that a pain-ameliorating effective daily dose is received by the subject. The daily dose may be given in divided doses as necessary, the precise amount of the compound received and the route of administration depending on the weight, age and sex of the patient being treated and on the particular disease condition being treated according to principles known in the art. A preferred dosage regime is once daily.

A further embodiment of the invention provides a pharmaceutical composition which contains a compound of the structural diagram I as defined herein or a pharmaceutically-acceptable salt thereof, in association with a pharmaceutically-acceptable additive such as an excipient or carrier.

A yet further embodiment of the invention provide the use of a compound of the structural diagram I, or a pharmaceutically-acceptable salt thereof, in the manufacture of a medicament useful for binding to the NMDA receptor glycine site in a warm-blooded animal such as a human being.

Still another embodiment of the invention provides a method of binding a compound of the invention to the NMDA receptor glycine site of a warm-blooded animal, such as a human being, in need of treatment for pain, which method comprises administering to said animal an effective amount of a compound of structural diagram I or a pharmaceutically-acceptable salt thereof.

Definitions:
Generally in the methods, processes and examples described herein:
concentrations were carried out by rotary evaporation in vacuo;
operations were carried out at ambient temperature, that is in the range 18–26° C. and under a nitrogen atmosphere;
column chromatography (by the flash procedure) was performed on Merck Kieselgel silica (Art. 9385) unless otherwise stated;
yields are given for illustration only and are not necessarily the maximum attainable;
the structure of the end-products of the formula I were generally confirmed by NMR and mass spectral techniques, proton magnetic resonance spectra were determined in DMSO-$d_6$ unless otherwise stated using a Varian Gemini 2000 spectrometer operating at a field strength of 300 MHz; chemical shifts are reported in parts per million downfield from tetramethylsilane as an internal standard (δ scale) and peak multiplicities are shown thus: s, singlet; bs, broad singlet; d, doublet; AB or dd, doublet of doublets; t, triplet, dt, double of triplets, m, multiplet; bm, broad multiplet; fast-atom bombardment (FAB) mass spectral data were obtained using a Platform spectrometer (supplied by Micromass) run in electrospray and, where appropriate, either positive ion data or negative ion data were collected, in this application, $(M+H)^+$ is quoted;
intermediates were not generally fully characterized and purity was in general assessed mass spectral (MS) or NMR analysis.

The following abbreviations and definitions when used, have the meanings, as follows:

| | |
|---|---|
| $CDCl_3$ | is deuterated chloroform; |
| CMC | is 1-cyclohexyl-3-(2-morpholinoethyl)carbodiimide metho-p-toluenesulfonate; |
| DCM | is dichloromethane; |
| DCU | is dicyclohexyl urea; |
| DHC | is 1,3-dicyclohexylcarbodiimide; |
| DMAP | is 4-(dimethylamino)pyridine; |
| DMF | is N,N-dimethylformamide; |
| DMSO | is dimethylsulphoxide; |
| m/s | is mass spectroscopy; |
| NMP | is N-methylpyrrolidinone; |
| NMR | is nuclear magnetic resonance; |
| p.o. | is per os; |
| THF | is tetrahydrofuran, and |
| t.i.d. | is three times daily. |

The examples and tests described herein are intended to illustrate but not limit the invention.

EXAMPLES

Example 1
(+/−)-7-chloro-4-hydroxy-2-(2H,3H,4H-Benzo[e]thian-4-yl)-1,2,5,10-tetrahydropyridazino[4,5-b]quinoline-1,10-dione.

N-(2H,3H-Benzo[e]thian-4-ylideneazamethyl)(tert-butoxy)carboxamide.

To a stirred solution of 2H,3H-benzo[e]thian-4-one (5.01 g, 30.5 mmol) in THF (200 mL) was added tert-butylcarbazate (6.12 g, 46.3 mmol) and 5 drops of concentrated hydrochloric acid. The resulting dark yellow solution was stirred at room temperature for 22 hr and then concentrated in vacuo to provide a beige solid (10.55 g). This solid was subjected to a Kugelrohr distillation (75° C., 10–20 millitorr) whereupon the unreacted tert-butylcarbazate was sublimed from the product. The residue in the distillation pot provided the title compound as a beige solid (7.19 g, 85%). $^1$H NMR (300 MHz, DMSO-$d_6$): δ 2.90 (t, 2H, J=6.0 Hz), 3.00 (t, 2H, J=6 Hz), 7.11–7.22 (m, 3H), 8.01 (d, 1H, J=7.8 Hz), 985 (s, 1H). MS (CI) m/z 279.

(+/−)-N-(2H,3H-Benzo[e]thian-4-ylamino)(tert-butoxy)carboxamide.

To a stirred solution of N-(2H,3H-benzo[e]thian-4-ylideneazamethyl)(tert-butoxy)carboxamide (6.33 g, 22.7 mmol) and sodium cyanoborohydride in methanol (500 mL) was added glacial acetic acid until the pH of the solution was 3. The resulting stirred solution was refluxed for 6 hr and then allowed to stand at room temperature overnight. The reaction mixture was concentrated in vacuo and the oily residue was suspended in saturated aqueous sodium bicarbonate. The pH of the resulting suspension was adjusted to 9–10 with sodium hydroxide and the mixture was extracted with ethyl acetate (5×125 mL). The combined organic extracts were dried ($Na_2SO_4$), filtered and concentrated to leave a clear thick oil which was purified by flash chromatography ($CH_2Cl_2$:MeOH gradient 100:0 to 90:10) over silica gel. The title compound was isolated as a clear oil (5.69 g, 89%). MS (CI) m/z 281.

Dimethyl 7-chloro-4-hydroxyquinoline-2,3-dicarboxylate:

A stirred mixture of methyl 2-amino-4-chlorobenzoate (2.50 g, 13.5 mmol) and dimethyl acetylenedicarboxylate (2.05 g, 14.4 mmol) in tert-butanol (22 ml) was refluxed for 7 hours under a nitrogen atmosphere. After adding additional dimethyl acetylenedicarboxylate (1.16 g, 8.13 mmol) and refluxing another 2.5 hours, the reaction mixture was allowed to cool to room temperature and potassium tert-butoxide (1.56 g, 13.9 mmol) was added in one portion. A precipitate formed and the resulting mixture was refluxed for 1.5 hours. The mixture was cooled to room temperature and filtered to separate the solids, which were washed with tert-butanol and diethyl ether. The solids were dissolved in water and acidified with 1 N sulfuric acid to form a precipitate. The resulting mixture was extracted with DCM and the combined extracts were washed with brine and water, dried over $MgSO_4$, filtered and concentrated to give a green solid. Recrystallization of this material from methanol provided the title compound (1.15 g, 47%) as an off-white solid, mp 232–233° C.; MS (Cl):296 (M+H). Analysis for $C_{13}H_{10}ClNO_5$: Calc'd: C, 52.81; H, 3.41; N, 4.74; Found: C, 52.75; H, 3.47; N, 4.69.

3-Carbomethoxy-7-chloro-4-hydroxyquinoline-2-carboxylic Acid:

To a stirred suspension of dimethyl 7-chloro-4-hydroxyquinoline-2,3-dicarboxylate (1.0 g, 3.38 mmol) in water (20 mL) was added an aqueous solution of sodium hydroxide (0.27 g, 6.75 mmol). Upon addition, the suspension dissolved. The reaction mixture was warmed to 60° C. for 1 hour. After this time the reaction was cooled to room temperature and acidified with concentrated hydrochloric acid. The product was then extracted into diethyl ether and ethyl acetate. The organic extracts were dried over $MgSO_4$, filtered and concentrated in vacuo to provide the title compound as a solid (900 mg). This material was purified by recrystallization employing an ethyl acetate/hexane co-solvent system to provide the title compound (571 mg, 60%) as a white solid mp 296° C. (dec); MS (CI)=238 (M+H). Analysis for $C_{12}H_8NO_5Cl.0.45 CH_3CO_2CH_2CH_3.0.10 H_2O$: Calc'd: C, 51.30; H, 3.68; N 4.34, Found: C, 51.28; H, 3.62; N 3.97 $^1$H NMR 8.22 (d, J=8.7 Hz, 1H), 7.92 (d, J=1.8 Hz, 1H), 7.28 (dd, J=8.7, 1.8 Hz, 1H), 3.90 (s, 3H).

3-Carbomethoxy-2-pyrrolidinocarbamide-7-chloro-4-hydroxyquinoline:

To a suspension of 3-carbomethoxy-7-chloro-4-hydroxyquinoline-2-carboxylic acid (2.25 g, 8.0 mmol) in THF (20 mL) at ambient temperature under a $N_2$ atmosphere was added DHC (1.65 g, 8.0 mmol) and pyrrolidine (0.596 g, 8.4 mmol). The reaction was stirred room temperature for 15 hours after which time the by-product urea was removed via filtration. The desired product was purified via flash column chromatography employing 5% methanol in chloroform to provide the title compound (2.52 g, 94.3%) as a tan solid, mp=215° C.; MS (CI): 335 (M+H). 300 MHz $^1$H NMR (DMSO-$d_6$): δ 8.12 (d, J=8.7 Hz, 1H), 7.60 (d, 1H, J=1.8 Hz), 7.47 (dd, 1H, J=8.8, 2.0 Hz), 3.69 (s, 3H), 3.40–3.49 (m, 2H), 3.27–3.33 (m, 2H), 1.80–1.96 (m, 4H).

7-Chloro-4-oxo-2-(pyrrolidinylcarbonyl)hydroquinoline-3-carboxylic acid:

To a suspension of 3-carbomethoxy-2-pyrrolidinocarbamide-7-chloro-4-hydroxy quinoline (2.52 g, 7.5 mmol) in de-ionized water (40 mL) was added dropwise a solution (20 mL) of an aqueous potassium hydroxide (882 mg, 15.75 mmol). Upon complete addition, the reaction was warmed to 60° C. After 3 hours, the reaction was filtered to remove a small amount of insoluble material. The filtrate was then acidified to pH=1 which yield a white precipitate. The solid was isolated by vacuum filtration, washed with water, and dried at 30° C. in vacuo for 16 hours. This provided the title compound (1.5 g, 64%) as a white solid, mp=225–8° C.; MS (CI): 321 (M+H). 300 MHz $^1$H NMR (DMSO-$d_6$): δ 8.28 (d, J=8.8 Hz, 1H), 7.77 (s, 1H), 7.64 (d, 1H, J=8.7), 3.52–3.57 (m, 2H), 3.17–3.19 (m, 2H), 1.83–1.98 (m, 4H).

(+/−)-N-{N-(2H,3H,4H-Benzo[e]thian-4-yl)[7-chloro-4-oxo-2-(pyrrolidinylcarbonyl)(3-hydroquinolyl)]carbonylamino}(tert-butoxy)carboxamide.

To a stirred suspension of 7-chloro-4-oxo-2-(pyrrolidinylcarbonyl)hydroquinoline-3-carboxylic acid (6.85 g, 21.4 mmol) and CMC (19.24 g, 45.42 mmol) in THF (100 mL) was added a THF (100 mL) solution of (+/−)-N-(2H,3H-benzo[e]thian-4-ylamino)(tert-butoxy)carboxamide (5.69 g, 20.3 mmol) followed by DMAP (~5 mg). The resulting bright yellow reaction mixture was stirred at room temperature overnight, refluxed for 2.5 hr, cooled and filtered. The collected solids were washed with THF and the above filtrate and washes were combined and concentrated in vacuo to provide a yellow foam (15.36 g). This material was partially purified by flash column chromatography ($CH_2Cl_2$:MeOH, 95:5) over silica gel to provide 10.22 g of a pale yellow solid. Final purification was carried out by stirring the solid in a DCM/methanol mixture (approximately 90:10) and collecting the undissolved white solid which was the title compound (5.15 g, 44%). MS (CI) m/z 583/585.

(+/−)-7-chloro-4-hydroxy-2-(2H,3H,4H-Benzo[e]thian-4-yl)-1,2,5,10-tetrahydropyridazino[4,5-b]quinoline-1,10-dione.

To a stirred solution of (+/−)-N-{N-(2H,3H,4H-benzo[e]thian-4-yl)[7-chloro-4-oxo-2-(pyrrolidinylcarbonyl)(3-hydroquinolyl)]carbonylamino}(tert-butoxy)carboxamide (5.15 g, 8.83 mmol) in THF (350 mL) was added methanesulfonic acid (29 mL, 42.9 g, 0.447 mole). A slight exothermic reaction occurred and the resulting bright yellow solution was stirred at room temperature and then at reflux for 5.5 hr. The reaction mixture was cooled to room temperature, poured into water (3L) and stirred overnight. The precipitate which formed was collected by filtration, suspended in methanol (20 mL), sonicated and filtered to separate a yellow solid (2.69 g). This material was again suspended in methanol (20 mL), sonicated and filtered to separate a yellow solid which was dried in vacuo to provide the title compound, mp>300° C. (2.42 g, 66%). $^1$H NMR (300 MHz, DMSO-$d_6$): δ 2.34 (m, 1H), 2.42 (m, 1H), 3.19 (m, 1H), 3.30 (m, 1H), 6.24 (dd, 1H, J=5.1, 14.4 Hz), 6.84 (d, 1H, J=7.5 Hz), 7.00 (m, 1H), 7.11 (m, 1H), 7.44 (d, 1H, J=8.7 Hz), 8.03 (d, 1H, J=1.8 Hz), 8.17 (d, 1H, J=8.7 Hz), 11.94 (s, 1H, exchangeable), 12.56 (s, 1H, exchangeable). Calc'd for $C_{20}H_{14}ClN_3O_3S·0.35 H_2O$: C, 57.45; H, 3.54; N, 10.05; Found: C, 57.02; H, 3.37; N, 10.46

Example 2

(+/−)-7-Chloro-4-hydroxy-2-(chroman-4-yl)-1,2,5,10-tetrahydropyridazino[4,5-b]quinoline-1,10-dione.

The title compound was prepared by the method described in Example 1 from 4-chromanone. Yield 63%; mp>300° C.; MS (CI) m/z 396/398; $^1$H NMR (300 MHz, DMSO-$d_6$): δ 2.17 (m, 1H), 2.36 (m, 1H), 4.31 (t, 1H, J=9.6 Hz), 4.44 (m, 1H), 6.34 (t, 1H, J=7.5 Hz), 6.83 (m, 3H), 7.12 (t, 1H, J=7.5 Hz), 7.44 (d, 1H, J=8.4 Hz), 8.02 (s, 1H), 8.17 (d, 1H, J=8.7 Hz), 11.93 (s, 1 H, exchangeable), 12.57 (s, 1 H, exchangeable); Calc'd for $C_{20}H_{14}ClN_3O_4·0.15 H_2O$ C, 60.28; H, 3.62; N, 10.51 Found: C, 60.10; H, 3.58; N, 10,86

Example 3

(+/−)-7-Chloro-4-hydroxy-2-(4,5,6,7-tetrahydrobenzo[b]thien-4-yl)-1,2,5,10-tetrahydropyridazino[4,5-b]quinoline-1,10-dione.

The title compound was prepared by the method described in Example 1 from 4-keto-4,5,6,7-tetrahydrothianaphthene. Yield 20%; mp>300° C.; MS (CI) m/z 400/402; $^1$H NMR (300 MHz, DMSO-$d_6$): δ 2.01 (m, 3H), 2.15 (m, 1H), 2.81 (m, 1H), 6.14 (m, 1H), 6.58 (d, 1H, J=5.1 Hz), 7.22 (d, 1H, J=5.1 Hz), 7.43 (d, 1H, J=8.1 Hz), 8.02 (d, 1H, J=1.5 Hz), 11.90 (s, 1H, exchangeable), 12.52 (s, 1H, exchangeable); Calc'd for $C_{19}H_{14}ClSN_3O_3·0.5 H_2O$ C, 55.82; H, 3.73; N, 10.23 Found: C, 55.83; H, 3.86; N, 10.18.

Example 4

(+/−)-7-Chloro-4-hydroxy-2-(1,2,3,4-tetrahydronaphth-1-yl)-1,2,5,10-tetrahydropyridazino[4,5-b]quinoline-1,10-dione.

The title compound was prepared by the method described in Example 1 from α-tetralone. Yield 83%; mp>300° C.; MS (CI) m/z 394/396; $^1$H NMR (300 MHz, DMSO-$d_6$): δ 1.90 (m, 1H), 2.07 (m, 3H), 2.81 (m, 2H), 6.25 (t, 1H, J=7.7 Hz), 6.81 (d, 1H, J=7.5 Hz), 7.11 (m, 3H), 7.44 (dd, 1H, J=1.8, 9.6 Hz), 8.03 (d, 1H, J=1.8 Hz), 8.17 (d, 1H, J=8.7 Hz), 11.91 (br s, 1 H, exchangeable), 12.50 (s, 1 H, exchangeable); Calc'd for $C_{21}H_{16}ClN_3O_3·0.7 H_2O$ C, 62.06; H, 4.32; N, 10.34 Found: C, 61.92; H, 4.21; N, 10.52

Tests for Biological Function:

Test A: Inhibition of Binding of [$^3$H]-MDL105,519:

Binding of compounds to the NMDA receptor glycine site may be assessed by measuring the ability of test compounds to inhibit the binding of tritiated MDL105,519 to brain membranes bearing the receptor.

Rat Brain Membranes: The rat brain membranes used in the experiments were obtained from Analytical Biological Services Inc., and were prepared substantially in accordance with the method of B. M. Baron et al., *J. Pharmacol. Exp. Ther.* 250, 162 (1989). Briefly, fresh brain tissue including cerebral cortex and hippocampus from mate Sprague Dawley rats was homogenized in 0.32 M sucrose and centrifuged at low speed to separate cellular membranes from other cellular components. The membranes were then washed 3 times using deionized water, followed by treatment with 0.04% Triton X-100. Finally, membranes were washed six times in 50 mM Tris citrate buffer, pH 7.4, and frozen at −80° C. until use.

[$^3$H]MDL105,519 (72 Ci/mmol) was purchased from Amersham. Cold MDL105,519 was purchased from Sigma/RBI. Binding assays were performed substantially in accordance with the protocol of B. M. Baron et al., *J. Pharmacol. Exp. Ther.* 279, 62 (1996), as follows. On the day of the experiment, brain membranes were thawed at room temperature and suspended in 50 mM tris acetate buffer, pH 7.4 ("TAB"). Seventy-five micro grams per milliliter protein (by using the BioRad dye) were used for competition binding. The experiments were carried out using 96-well plates. Membranes were incubated with 20 μL of compounds of various concentrations and 1.2 nM [$^3$H]MDL105,519 for 30 minutes at room temperature in a total volume of 250 μL. Non specific binding was determined by using 100 μM of unlabeled MDL105,519. The unlabeled MDL105,519 and compounds were dissolved as 12.5 mM stock solutions in DMSO. Final DMSO concentration in each well was kept below 1%, which concentration was found not to alter the binding results. After incubation, unbound [$^3$H]MDL105,519 was removed by filtration onto GF/B Unifilter plates using a Packard harvester. Filters were washed four times with ice cold TAB (total of 1.2 mL buffer). The plates were dried overnight at room temperature and bound radioactivity was measured on a Packard TopCount after the addition of 45 μL per well of the MICROSCINT O.

Human Brain Membranes: Human brain membranes were obtained from Analytical Biological Services Inc., and assays were performed as described for rat membranes.

Data analysis: Data was analyzed using a Microsoft Excel spreadsheet and GraphPad Prizm software and potency of compounds is expressed as the Ki (nM).

Test B: Formalin Test:

The Formalin test is an assay that assesses the capacity of a compound to inhibit formalin-induced nociceptive behaviors in rats (D. Dubuisson, et al., *Pain* 4, 161–174 (1977); H. Wheeler-Aceto et al., *Psychopharmacology* 104, 35–44 (1991); T. J. Coderre, et al., *Pain* 54, 43–50 (1993)). In the test, two distinctive phases of formalin-induced behaviors are observed. A first phase response, caused by acute nociception to the noxious chemical (formalin) injected into the paw, occurs between zero and five minutes. A quiescent period of 5 to 15 min post injection follows. After the quiescent period a second phase response, caused by sensitization of the central neurons in the dorsal horn, occurs after 15 minutes and lasts up to 60 minutes. Sensitization of the central neurons in the spine augments a noxious afferent input and causes a stronger pain barrage to be transmitted to the brain. Therefore, inhibition of the second phase response indicates a central mechanism of drug action.

The procedure for the formalin test may be performed as follows: male rats are placed in a plexiglass chamber and observed for 30–45 min. to observe their baseline activity. Animals would either be pretreated with vehicle or with different doses of a test compound and are dosed with vehicle or test compound three hours prior to injection of 0.05 mL of sterile 1% formalin under the dorsal skin of a hind paw. The number of paw flinches (responses) during the first phase (0–5 min.) and the second phase (20–35 min.) are scored and recorded. Flinch response can be compared with the mean score of a saline control group and calculated as percentage inhibition. The $ED_{50}$ is the dose of compound which produced 50% inhibition of nociceptive response in the first or second phase response.

% inhibition of nociceptive response can be calculated as:

$$100 \times \frac{\text{(number of responses in vehicle group} - \text{number of responses in compound group)}}{\text{(number of responses in vehicle group)}}$$

Student's t-test can be used for statistical analysis to determine the significance of compound effects.

Test C: Neuropathic Pain Model (Chronic Constriction Injury):

The anti-hyperalgesic properties of a compound may be tested with the Chronic Constriction Injury ("CCI") model. The test is a model for neuropathic pain associated with nerve injuries that can arise directly from trauma and compression, or indirectly from a wide range of diseases such as infection, cancer, metabolic conditions, toxins, nutritional deficiencies, immunological dysfunction, and musculoskeletal changes. In the model a unilateral peripheral hyperalgesia is produced in rats by nerve ligation (G. J. Bennett, et al., *Pain* 33, 87–107 (1988)).

Procedurally, Sprague-Dawley rats (250–350 g) are anesthetized with sodium pentobarbital and the common sciatic nerve is exposed at the level of the mid thigh by blunt dissection through the biceps femoris. A section of nerve (about 7 mm), proximal to the sciatic trifucation, is freed of tissue and ligated at four positions with chromic gut suture. The suture is tied with about 1 mm spacing between ligatures. The incision is closed in layers and the animals are allowed to recuperate. Thermal hyperalgesia is measured using a paw-withdrawal test (K. Hargreaves, et al., *Pain* 32, 77–88 (1988)). To perform the test, animals are habituated on an elevated glass floor. A radiant heat source is aimed at the mid-plantar hindpaw (sciatic nerve territory) through the glass floor with a 20 second cut-off used to prevent injury to the skin. The latencies for the withdrawal reflex in both hind paws are recorded.

Injured paws with ligated nerves show shorter paw withdrawal latencies compared to the uninjured or sham operated paws. Responses to test compounds are evaluated at different times after oral administration to determine the onset and duration of compound effect. When performing the test, groups of CCI rats receive either vehicle or the test compound orally three times daily for 5 days. Paw withdrawal latencies are measured each day 10 min before and 2 or 3 hr. after the first daily dose. Compound efficacy is expressed as mean percentage decrease of hyperalgesia compared to that of vehicle-treated animals, calculated as follows:

$$\frac{\text{(Mean of vehicle group} - \text{Mean of compound group)}}{\text{(Mean of vehicle group)}} \times 100$$

Data analysis was performed by the multiple means comparison test (Dunnett's test) and results are expressed and compound potencies are expressed as the MED (minimum effective dose), in mg/Kg/day, that yields a percent (%) decrease in hyperalgesia that is statistically significant.

Table 1 shows the results from Tests A and C for certain compounds of the invention. Where no data is provided in the table, the test was not performed.

TABLE 1

|  | Test A Ki (nM) | Test C MED (% Inh.) |
|---|---|---|
| Ex. 1: | 411 | 30 (56%) |
| Ex. 2: | 557 |  |
| Ex. 3: | 514 |  |
| Ex. 4: | 725 |  |

What is claimed is:
1. A compound in accord with structural diagram I,

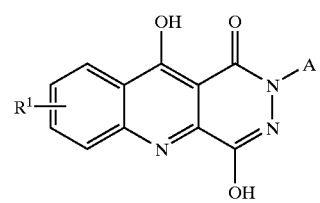

or a tautomer thereof wherein:

$R^1$ is halo;

A is selected from groups according to structural diagrams II, III, IV and V

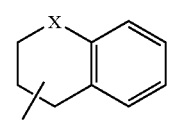

II

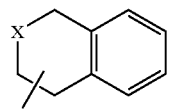

III

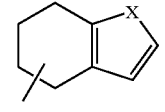

IV

-continued

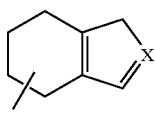
V wherein X is selected from carbon, oxygen and sulfur, or pharmaceutically-acceptable salts thereof.

2. A compound according to claim 1, according to structural diagrams VI or VII

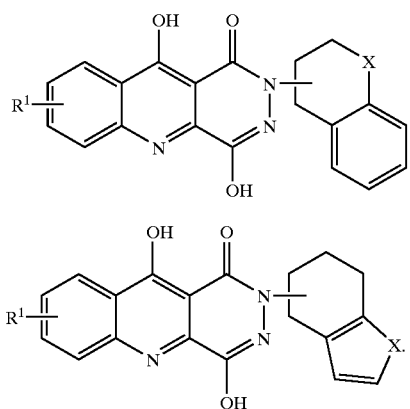

3. A compound according to claim 2, according to structural diagrams VIII or IX:

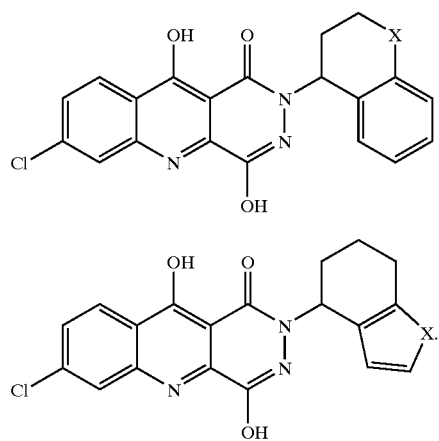

4. A compound according to claim 3, selected from:
7-chloro-4-hydroxy-2-(2H,3H,4H-Benzo[e]thian-4-yl)-1,2,5,10-tetrahydropyridazino[4,5-b]quinoline-1,10-dione;
7-chloro-4-hydroxy-2-(chroman-4-yl)-1,2,5,10-tetrahydropyridazino[4,5-b]quinoline-1,10-dione;
7-chloro-4-hydroxy-2-(4,5,6,7-tetrahydrobenzo[b]thiophen-4-yl)-1,2,5,10-tetrahydropyridazino[4,5-b]quinoline-1,10-dione, and
7-chloro-4-hydroxy-2-(1,2,3,4-tetrahydronaphthyl)-1,2,5,10-tetrahydropyridazino[4,5-b]quinoline-1,10-dione.

5. A method for treating a subject suffering from pain comprising administration of a pain-ameliorating effective amount of a compound according to structural diagram I,

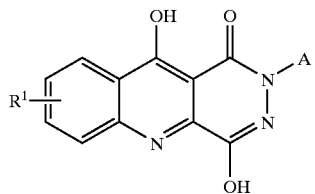
I or a tautomer or a pharmaceutically-acceptable salt thereof wherein:

$R^1$ is halo;

A is selected from groups according to structural diagrams II, III, IV and V

II

III

IV

V wherein X is selected from carbon, oxygen and sulfur.

6. A method according to claim 5, comprising administration of a compound according to structural diagrams VI or VII

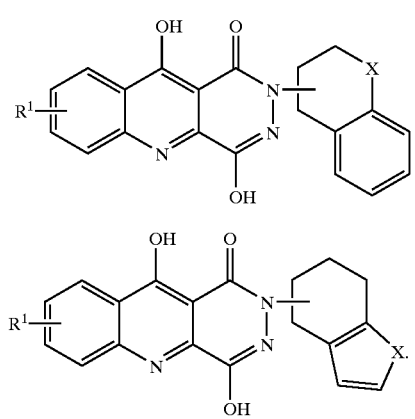

7. A method according to claim 6, comprising administration of a compound according to structural diagrams VIII or IX:

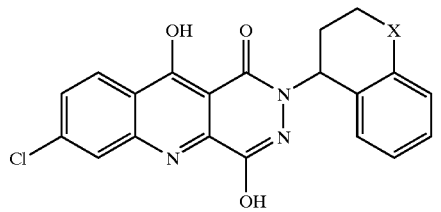

VIII

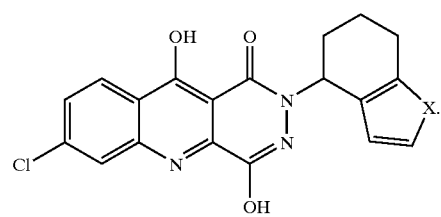

IX

8. A method according to claim 7, comprising administration of a compound selected from:

7-chloro-4-hydroxy-2-(2H,3H,4H-Benzo[e]thian-4-yl)-1,2,5,10-tetrahydropyridazino[4,5-b]quinoline-1,10-dione;

7-chloro-4-hydroxy-2-(chroman-4-yl)-1,2,5,10-tetrahydropyridazino[4,5-b]quinoline-1,10-dione;

7-chloro-4-hydroxy-2-(4,5,6,7-tetrahydrobenzo[b]thiophen-4-yl)-1,2,5,10-tetrahydropyridazino[4,5-b]quinoline-1,10-dione, and 7-chloro-4-hydroxy-2-(1,2,3,4-tetrahydronaphthyl)-1,2,5,10-tetrahydropyridazino[4,5-b]quinoline-1,10-dione.

9. A pharmaceutical composition comprising a pain-ameliorating effective amount of a compound according to structural diagram I,

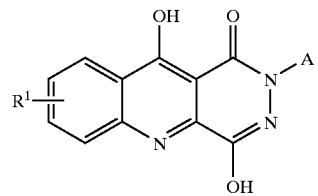

I or a tautomer or a pharmaceutically-acceptable salt thereof wherein:
  $R^1$ is halo;
  A is selected from groups according to structural diagrams II, III, IV and V

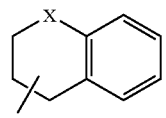

II

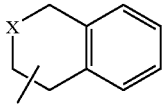

III

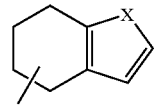

IV

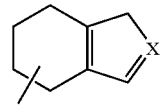

V wherein X is selected from carbon, oxygen and sulfur, together with a pharmaceutically-acceptable excipient or diluent.

* * * * *